United States Patent [19]
Erman et al.

[11] Patent Number: 6,160,182
[45] Date of Patent: Dec. 12, 2000

[54] PROCESS FOR OBTAINING MIXTURES OF ISOMERIC ACYLOCTAHYDRONAPHTHALENES

[75] Inventors: Mark B. Erman, Atlantic Beach; Carlos G. Cardenas; Henri M. Hoffmann, both of Jacksonville, all of Fla.

[73] Assignee: Millennium Specialty Chemicals, Jacksonville, Fla.

[21] Appl. No.: 09/136,448

[22] Filed: Aug. 19, 1998

[51] Int. Cl.[7] .................................................. C07C 45/67
[52] U.S. Cl. ........................... 568/347; 568/343; 568/443
[58] Field of Search .................................... 568/343, 347, 568/374, 377, 443

[56] References Cited

U.S. PATENT DOCUMENTS

| | | | |
|---|---|---|---|
| 2,815,379 | 12/1957 | Surmatis et al. | 260/587 |
| 2,933,506 | 8/1960 | Ohloff et al. | 260/343.2 |
| 3,907,321 | 9/1975 | Hall et al. | 131/17 R |
| 3,911,018 | 10/1975 | Hall et al. | 260/586 C |
| 3,929,677 | 12/1975 | Hall et al. | 252/522 |
| 4,250,338 | 2/1981 | Sprecker et al. | 568/343 |
| 5,214,160 | 5/1993 | Ertzweiler et al. | 547/290 |
| 5,707,961 | 1/1998 | Baggrowicz et al. | 512/17 |

FOREIGN PATENT DOCUMENTS

| | | |
|---|---|---|
| 464357B1 | 1/1992 | European Pat. Off. . |
| 743297A1 | 11/1996 | European Pat. Off. . |
| 40992 | 2/1994 | Japan . |
| 896039 | 5/1962 | United Kingdom . |

OTHER PUBLICATIONS

Yuan and Peng, Chinese Chemical Letters, vol. 3, No. 7, pp. 507–510 (1992).

G. Fráter et al., 213th ACS National Meeting San Francisco, Apr. 13–17, Books of Abstracts, Part 2, p. 147 (1997).

*Primary Examiner*—Sreeni Padmanabhan
*Attorney, Agent, or Firm*—Needle & Rosenberg, P.C.

[57] ABSTRACT

Acid catalyzed cyclization of Diels-Alder adducts of myrcene is performed in the presence of hydroxyl-containing compounds, giving the resulting mixtures of isomeric acyloctahydronaphthalenes enhanced quantities of isomers that are particularly useful in perfumery because of their woody-amber odors with enhanced amber note.

20 Claims, No Drawings

PROCESS FOR OBTAINING MIXTURES OF ISOMERIC ACYLOCTAHYDRONAPHTHALENES

FIELD OF THE INVENTION

The invention relates to methods for preparing compounds useful in perfumery, particularly to methods for preparing mixtures of isomeric acyloctahydronaphthalenes.

BACKGROUND OF THE INVENTION

Mixtures of isomeric acyloctahydronaphthalenes of generic formulas 1, often containing minor concentrations of isomers of generic formula 2 and other structural isomers, are commonly obtained by the acid-catalyzed cyclization of corresponding Diels-Alder adducts of generic formula 3. Diels-Alder adducts 3 are obtained by reacting myrcene with appropriately substituted α,β-unsaturated carbonyl compounds (Scheme 1). The wavy lines in formulas 1 and 2 represent possible positions of the one double bond; $R^1$ is a hydrogen atom or an alkyl group, $R^2$ is a hydrogen atom or an alkyl group, $R^3$ is an alkyl group.

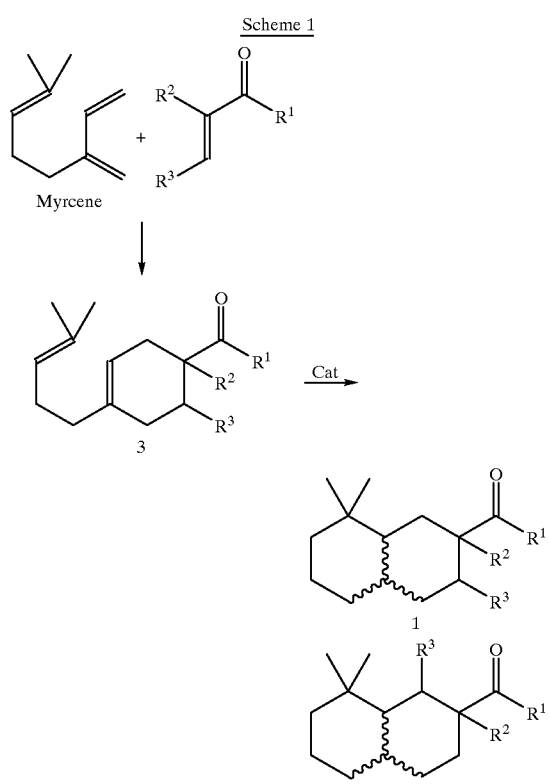

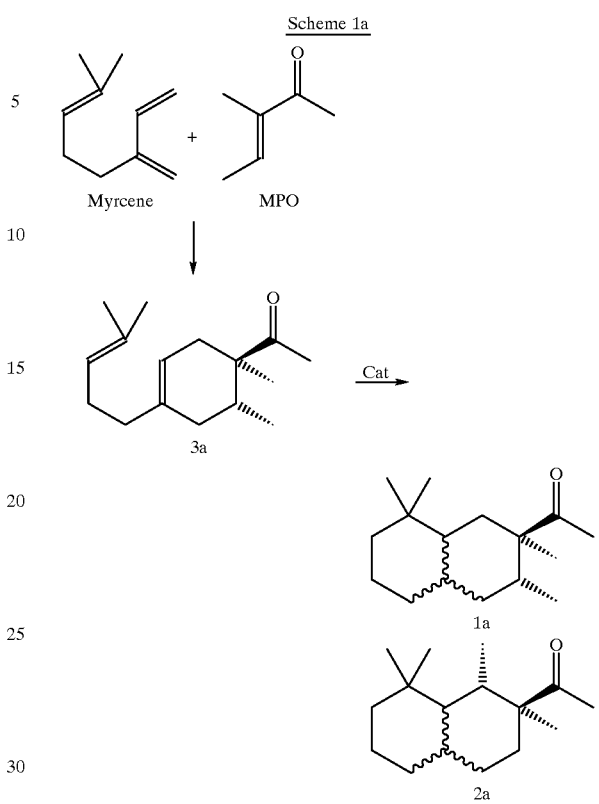

The cyclization of the Diels-Alder adduct 3a, wherein $R^1=R^2=R^3=CH_3$, is the most important from the practical standpoint. Isomeric mixtures of acetyl octahydronaphthalenes thus obtained (Scheme 1a) are well-known in the prior art as woody-amber and fruity-amber odorants. The compounds 1a, 2a, 3a are generally present as racemic mixtures, although only one enantiomer is shown for each of them in Scheme 1a. Similarly, when only one enantiomer is shown for compounds in other schemes of this document, such compounds are typically present as racemic mixtures.

Odor quality of such mixtures depends on their isomeric composition, which in turn depends on the method used to cyclize the Diels-Alder adduct 3a. However, until now there has been a lack of information on how the cyclization method affects the isomeric composition, and even on the actual composition of the reported isomeric mixtures. Furthermore, information obtained from some sources is questionable.

For example, G. Ohloff in the article "Chemistry of Odoriferous and Flavoring Substances" in the book "Fortschritte der Chemischen Forschung", 1969, Bd.12/2, S.192, disclosed a compound of formula 1a-α having the double bond at the location shown in the 1a-α structure in Scheme 2, and indicated that materials of this nature have "resiny odors" like olibanum, with amber type undertones. The article did not give any information on the origin of this material or how it was prepared.

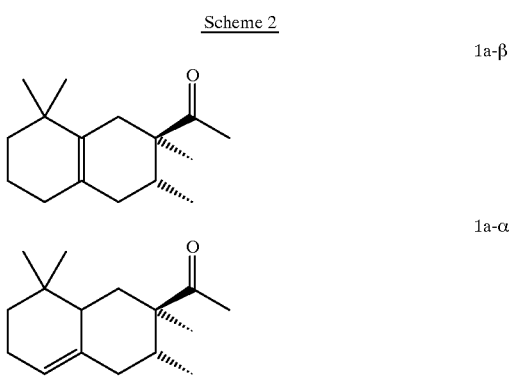

1a-γ

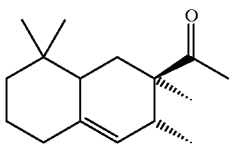

U.S. Pat. Nos. 3,907,321, 3,911,018, and 3,929,677 disclose the cyclization of the Diels-Alder adduct 3a in the presence of Brönsted acids (such as phosphoric and sulfuric acids), preferably in the presence of an inert solvent (toluene). According to these three patents, cyclization of the Diels-Alder adduct 3a in the presence of 85% phosphoric acid in toluene at 70–80° C. gives, after work-up and distillation, an 86.8% yield of a mixture of isomers possessing an amber aroma. GLC analysis of the product showed two major peaks: 93% of 1a-β isomer, and 7% of the 1a-α isomer (and/or 1a-γ isomer). After isolation by preparative GLC, the 1a-β isomer had a "slight buttery note with a strong woody amber character", and the 1a-α isomer (and/or 1a-γ isomer)—"weak, low-keyed with a green vegetable character".

U.S. Pat. Nos. 3,907,321, 3,911,018, and 3,929,677 also disclose using Lewis acids as cyclization catalysts, and contain an example wherein the Diels-Alder adduct 3a is cyclized in the presence of boron trifluoride etherate in toluene. However, the patents do not report yield or product composition from the cyclization.

Russian authors (V. M. Andreev et al., "Pischevaya Promyshlennost", 1990, N 11, p.55–56) cyclized the Diels-Alder adduct 3a at 115–120° C. (in toluene) in the presence of small amounts of phosphoric acid. They found that the product (mainly 1a-β isomer), had a tenacious woody-amber odor with a "velvet" nuance. However, the yield of cyclized product was only 63%. The article mentions the formation of an impurity adversely affecting the odor. The authors subsequently identified the impurity as 1,2,4,9,11-pentamethyl-3-oxatetracyclo[6.2.2.0$^{2,8}$.0$^{4,9}$]dodecane—a by-product resulting from the secondary cyclization of the 1a-β isomer (V. M. Andreev et al., Zh. Org. Khim., 1991, V.27(2), pp.413–414 [CA 115:183058].

Japanese Kokai 6[1994]-40,992 gives the following odor gradation for 1a-α, 1a-β, and 1a-γ isomers, but contains no evidence that the isomers were isolated, or any indication of how the isomers were characterized, which makes this gradation questionable:

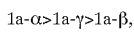

where ">" means "better".

According to this Kokai, cyclization with Amberlyst-15 (an acidic sulfonated ion-exchange resin) gives better results than cyclization using phosphoric, sulfuric, and p-toluenesulfonic acids. However, continuous cyclization with Amberlyst-15, yielded only 82.1% of the product, or almost 5% lower than in the above mentioned U.S. patents using phosphoric acid, and the Kokai gave no information on the concentration of unreacted starting material. Moreover, the example reveals significant difficulties in controlling the conversion of the Diels-Alder adduct 3a and the isomer ratio at the same time. Batch format allowed better control of conversion, and less than 2% of unreacted starting material remained, but the yield was significantly lower (74.2%). Lower yields, difficulties of control in the continuous version, and other disadvantages such as mechanical friability of catalyst and large ratio of catalyst to substrate (0.7) in the batch version, make heterogeneous catalysis by Amberlyst-15 unattractive.

A one-pot version of the Diels-Alder reaction of myrcene and MPO to produce the Diels-Alder adduct 3a, and its subsequent cyclization in the presence of a Lewis acid (not specified) was published in "Chinese Chemical Letters", 1992, Vol.3, N 7, pp.507–510. The main product (1a-β isomer) was purified via its semicarbazone, and its structure was rigorously proven by $^1$H and $^{13}$C NMR spectroscopy, including 2D $^1$H (H—H COSY) and 2D $^{13}$C (C—H COSY) versions. No odor description was given and no yield reported.

The first publication concerning the synthesis of compounds of generic formula 2a appeared in Bull. Soc. Chim. France, 1959, pp. 601–606 (M. Mousseron-Canet et al.). Recently it was found that the protocol of Mousseron-Canet does not give compounds of generic formula 2a, but instead gives other types of structures (see EP 743297 and U.S. Pat. No. 5,707,961).

The aforementioned EP 743297 and U.S. Pat. No. 5,707,961 disclose compounds of generic formula 4 (as shown in Scheme 3) as odorants, including a mixture of compounds 4-1 and 4-2 (with Me groups trans to one another) with amber-woody and tobacco odor. The mixture of compounds 4-1+4-2 was obtained by the Grignard methylation of citral, dehydration of the Grignard product by iodine into methylmyrcene, and Diels-Alder reaction of methylmyrcene with methyl isopropenyl ketone followed by the cyclization of the adduct.

Scheme 3

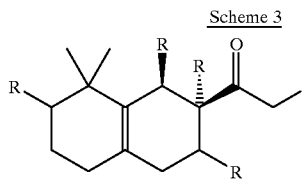

4

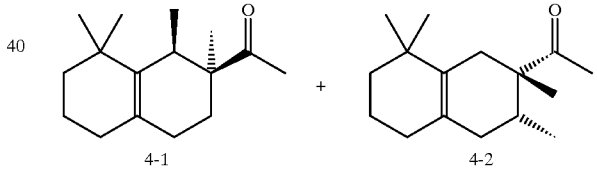

4-1    4-2

EP 743297 also mentions that a compound having structure 2a with cis-methyl groups, namely the 2a-β isomer, is practically odorless. EP 743297 states that the 2a-β isomer can be obtained by the acid-catalyzed isomerization of the corresponding 2a-γ isomer (Scheme 4). EP 743297 does not give the procedure for the isomerization or give spectral data to confirm the structure.

Scheme 4

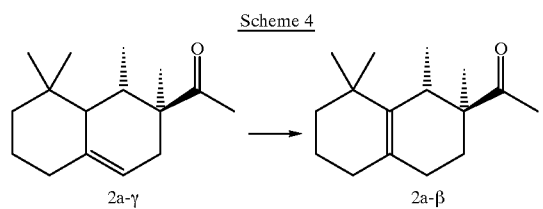

2a-γ    2a-β

A sophisticated multi-step synthesis of the 2a-γ isomer from α-ionone according to the Scheme 5 below was disclosed in EP 464357, and U.S. Pat. Nos. 5,180,709, and 5,214, 160.

Scheme 5

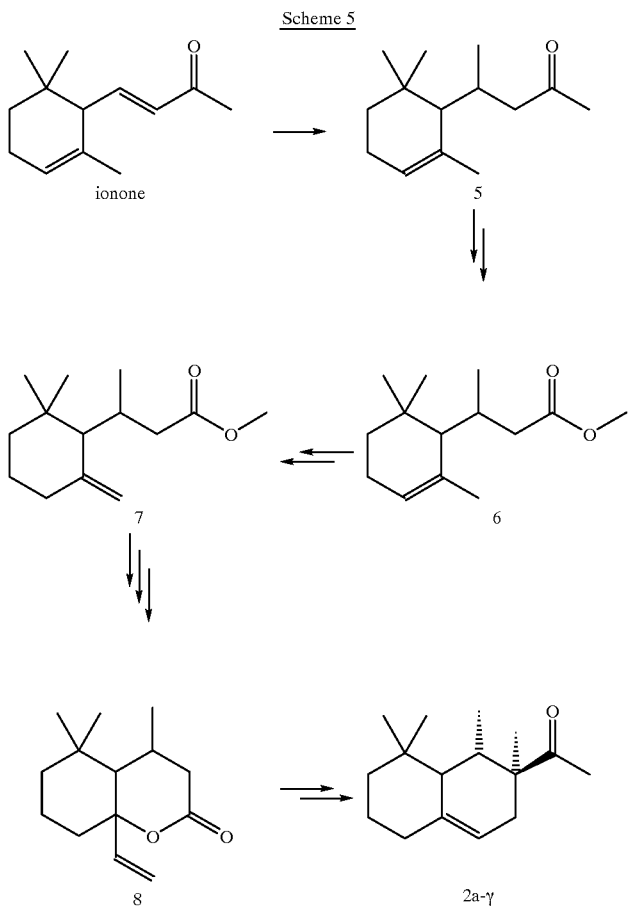

According to this method, α-ionone is transformed into methyldihydroionone 5 by reaction with dimethyl CuLi. Next, methyldihydroionone 5 is converted into ester 6 by the haloform reaction and esterification. Ester 6 is reacted with NaOCl, and then ozonized and treated with $Zn/H_2O$ to give ketoester 7. The latter is converted into lactone 8 by addition of acetylene-MgBr (with spontaneous cyclization) followed by partial hydrogenation of the triple bond. After introduction of a methyl group by LDA/MeI, the product is silylated (BuLi/Me$_3$SiCl), isomerized (reflux in toluene; Ireland-Claisen rearrangement) and methylated again (MeLi/ether) to give the 2a-γ isomer. The structure of the 2a-γ isomer was proven on the basis of its NMR spectra.

These patents state that the 2a-γ isomer possesses a very powerful amber woody odor, with an enormously low odor threshold value (5 pg/l air) compared to the 1a-β isomer, which has a threshold value of 500 ng/l (100,000 times). In "Perfumes. Art, Science, Technology" [P. M. Müller and D. Lamparsky, eds. Blackie Academic & Professional, London-New-York-Tokyo-Melbourne-Madras, 1994, p.197] the 2a-γ isomer was also mentioned as having a powerful woody amber-like note with an odor threshold of about 3 pg/l.

Finally, it was found that the 2a-γ isomer appears as a "minor side product" in the acid catalyzed cyclization of Diels-Alder adduct 3a of myrcene and (E)-3-methylpent-3-en-2-one (MPO) [G. Fráter et al. 213th ACS National Meeting San-Francisco, Calif., Apr. 13–17, 1997. Books of Abstracts, Part 2, p.147].

There is even less information regarding the cyclization of Diels-Alder adducts of generic formula 3 other than 3a.

British Pat. No. 896,039 claims a method of producing derivatives of octahydronaphthalene wherein a compound of the general formula:

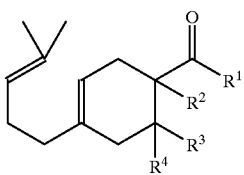

in which $R^2$, $R^3$, and $R^4$ are hydrogen atoms, or alkyl groups, and in which $R^1$ is a hydroxy, alkyl, or alkoxy group, or in which $R^1$ is a hydrogen atom and the compound is in the form of a Schiff base, is cyclized with phosphoric acid, or boron trifluoride, or mixtures thereof, at a temperature between −30° C. and +75° C., or is cyclized with sulfuric acid or formic acid, or mixtures thereof, at a temperature between −30° C. and +10° C. The patent does not contain examples which could be considered in conjunction with the present document.

Cyclization of the Diels-Alder adduct 3b ($R^1$=$R^2$=H; $R^3$=Me) in the form of its Shiff's base was described in G. Ohloff, Liebigs Annalen der Chemie, 1957, Bd. 606, S. 100–123 (see pages 112 and 116), and also in U.S. Pat. No. 2,933,506, wherein the Shiff base was cyclized at −15° C. in the presence of a large excess of 62% sulfuric acid.

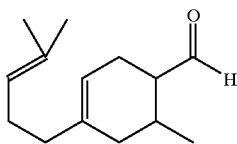
3b

Cyclization of the Diels-Alder adducts 3c ($R^1$=Et; $R^2$=H; $R^3$=Me) and 3d ($R^1$=H; $R^2$=Me; $R^3$=Et), was mentioned in U.S. Pat. Nos. 3,911,018 and 3,929,677 as giving respectively products with "green, buttery, woody", and "fruity, woody, pineapple-like and ionone-like" odors. According to these U.S. patents, the cyclization was conducted using the procedure given in British patent no. 896,039. However, the U.S. Pat. Nos. 3,911,018 and 3,929,677 did not give information on the yields and details of the procedure.

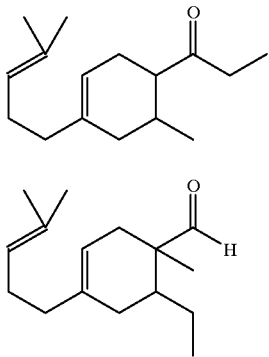

3c

3d

Thus, it is known that:
1. Mixtures of isometric acetyloctahydronaphthalenes obtained by the acid-catalyzed cyclization of the Diels-Alder adduct 3a contain 1a-β isomer as the major constituent, and the 2a-γ isomer as a minor side product. Available information on the odor, presence, structures and concentrations of other constituents is insufficient;
2. Odor strength and odor quality of such mixtures may depend largely on the concentration of the minor 2a-γ side product because of its enormously low odor threshold (3–5 pg/l vs. 500 ng/l for the major 1a-β isomer); and
3. Cyclization by-product 1,2,4,9,11-pentamethyl-3-oxatetracyclo[$6.2.2.0^{2,8}.0^{4,9}$]-dodecane (POD) adversely affects the odor of such mixtures.

SUMMARY OF THE INVENTION

We have now unexpectedly discovered that when the acid catalyzed cyclization of compound 3a is performed in the presence of hydroxyl-containing compounds, the resulting mixtures of isomeric acetyloctahydronaphthalenes advantageously contain enhanced quantities of the 2a-γ isomer. The process also provides mixtures containing lesser amounts of the by-product 1,2,4,9,11-pentamethyl-3-oxatetracyclo[$6.2.2.0^{2,8}.0^{4,9}$]-dodecane (POD) and gives yields of cyclized product that are higher than the yields reported in the prior art.

An additional advantage of the invention is that after the cyclization process is complete, the acid catalyst and hydroxyl-containing compound are present as a distinct bottom layer and can thus be easily separated and reused repeatedly, thereby minimizing washings and waste water.

The compositions produced according to the invention are particularly useful in perfumery because they possess woody-amber odors with an enhanced amber note.

Thus, in one aspect the invention provides a process for obtaining isomeric compounds represented by formulas 1 and 2, comprising contacting a composition comprising a compound represented by formula 3 with an acid catalyst and a hydroxyl-containing compound ROH or RCOOH, wherein:

a. formulas 1, 2, and 3 are as shown below:

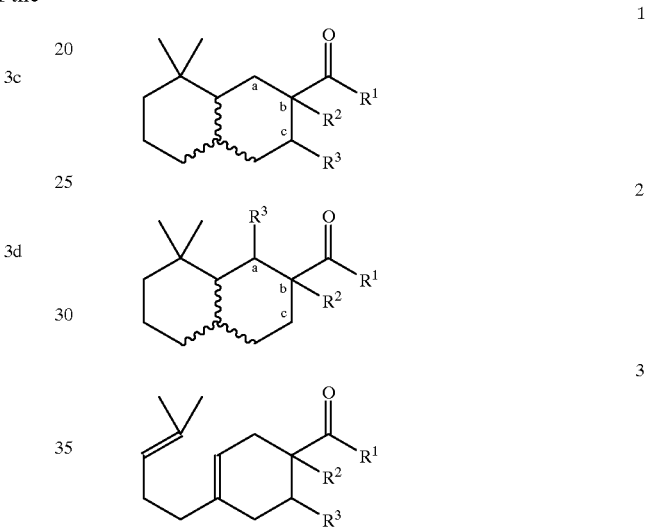

b. one of the wavy lines in each of formulas 1 and 2 represents a double bond, and the two other wavy lines represent a single bond;
c. R is a linear or cyclic alkyl group, or hydroxyalkyl group, or alkoxyalkyl group, or aryl group, and is substituted or unsubstituted, saturated or unsaturated;
d. $R^1$ and $R^2$ are independently hydrogen or lower alkyl;
e. $R^3$ is lower alkyl; and
f. the configuration at carbon b and c in formula 1, and a and b in formula 2, is independently R or S.

In another aspect the invention provides a process for obtaining isomeric compounds represented by formulas 1 and 2, comprising contacting a composition comprising a compound represented by formula 12 with an acid catalyst, wherein:

a. formulas 1, 2, and 12 are as shown below:

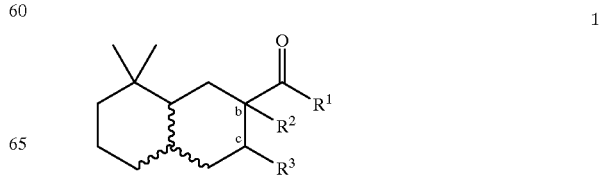

-continued

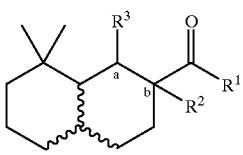

2

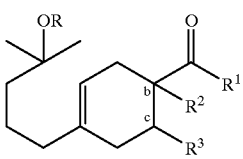

12 b. one of the wavy lines in each of formulas 1 and 2 represents a double bond, and the two other wavy lines represent a single bond;
c. R is a linear or cyclic alkyl group, or hydroxyalkyl group, or alkoxyalkyl group, or aryl group, and is substituted or unsubstituted, saturated or unsaturated;
d. $R^1$ and $R^2$ are independently hydrogen or lower alkyl;
e. $R^3$ is lower alkyl;
f. the configurations at carbon b and c in structures 1 and 12, and a and b in structure 2 are independently R or S.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Discussion

The present invention may be understood more readily by reference to the following discussion and the examples which follow. However, before the present compounds, compositions and methods are disclosed and described, it is to be understood that this invention is not limited to specific compositions or compounds, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an isomer" includes mixtures of isomers, reference to "an alcohol" includes mixtures of two or more such alcohols, and the like.

Ranges are often expressed herein as from "about" one particular value, and/or to "about" another particular value. When such a range is expressed, it is to be understood that another embodiment is typically from the one particular value and/or to the other particular value. Similarly, when values are expressed as approximations, by use of the antecedent "about," it will be understood that the particular value is another embodiment.

In this specification, and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "lower alkyl" intends an alkyl group of from one to three carbon atoms.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

In one embodiment the invention provides a process for obtaining isomeric compounds represented by formulas 1 and 2 in Scheme 6. The process comprises contacting a composition comprising a compound represented by formula 3 with an acid catalyst and a hydroxyl-containing compound ROH or RCOOH, wherein:
a. formulas 1, 2, and 3 are as shown below in Scheme 6:

Scheme 6

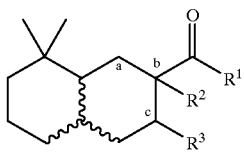

1

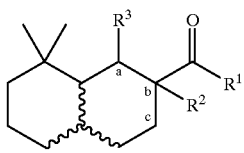

2

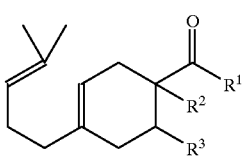

3 b. one of the wavy lines in each of formulas 1 and 2 represents a double bond, and the two other wavy lines represent a single bond;
c. R is a substituted or unsubstituted, saturated or unsaturated, linear or cyclic alkyl group, or hydroxyalkyl group, or alkoxyalkyl group, or aryl group;
d. $R^1$ and $R^2$ are independently hydrogen or lower alkyl;
e. $R^3$ is lower alkyl; and
f. the configurations at carbons b and c in structure 1 and a and b in structure 2 are independently R or S.

As recognized in the art, the symbol—represents a covalent bond site terminated by a methyl moiety.

As shown in Scheme 6, and as discussed previously, compound 3 in one embodiment is the Diels-Alder adduct of myrcene and MPO. However, compounds that are structurally related to MPO, such as crotonaldehyde, 4-hexen-3-one, and 2-methyl-2-pentenal can also be used to prepare compound 3, as shown in the general structure for compound 3 in scheme 6. In a preferred embodiment $R^1$ is methyl. In a more preferred embodiment compound 3 is the Diels-Alder adduct of myrcene and MPO, and $R^1$, $R^2$, and $R^3$ are methyl.

Numerous R moieties can be selected for the ROH or RCOOH compound. In the embodiment discussed above R is a substituted or unsubstituted, saturated or unsaturated, linear or cyclic alkyl group, or hydroxyalkyl group, or alkoxyalkyl group. Thus, ROH can contain other functional groups and/or unsaturated hydrocarbon chains, branched or linear. R is preferably branched or linear lower alkyl. Preferably, but not necessarily, ROH or RCOOH is well soluble in water and in aqueous solutions of acids.

In a preferred embodiment compound ROH is methanol, ethanol, 1-propanol, 2-propanol, a 2-alkoxyethanol, an alkoxypropanol, ethylene glycol, a propylene glycol, or a mixture thereof. Even more preferably ROH is a lower alkanol such as methanol, ethanol, isopropanol, or propanol. In another embodiment the hydroxyl-containing compound is a diol or polyol, or a monoalkyl ether of a diol such as methyl cellosolve.

If RCOOH is used, it can be used by itself or in combination with ROH. Preferred RCOOH compounds include acetic acid, propanoic acid, butyric, isobutyric, hexanoic acid, benzoic acid, oxalic acid, and glutaric acid. A particularly preferred RCOOH is acetic acid.

The process can be carried out with a great variety of acid catalysts or mixtures of acid catalysts, including any acid catalyst known in the art for cyclizing Diels-Alder adducts. The acid catalyst is a separate compound from RCOOH, although a related carboxylic acid, HCOOH (formic acid), can be used as the acid catalyst. In one embodiment the acid catalyst is any Lewis or Brönsted acid other than a carboxylic acid. In another embodiment the acid catalyst is any Lewis or Brönsted acid other than RCOOH. In still another embodiment the acid catalyst is a Brönsted acid, or a mixture of Brönsted acids, but typically the acid catalyst is a solution of one or more Brönsted acids in water. Preferred Brönsted acids are either organic or inorganic, and include phosphoric, sulfuric, benzenesulfonic, p-toluenesulfonic, and sulfosalicylic acids. Other exemplary acid catalysts are the esters of diacids such as, for example, monomethyl sulfate. In another embodiment the acid catalyst is a Lewis acid or the aqueous solution of a Lewis acid complex, or a mixture thereof. A particularly suitable Lewis acid catalyst is boron trifluoride, its ether complex or its methanol complex.

The method optionally comprises the additional step of separating the acid catalyst and ROH or RCOOH from the mixture of isomers after sufficient conversion. The acid catalyst and ROH or RCOOH can then be reused in subsequent reactions. Prior art processes have carried out the reaction in the presence of inert solvents such as toluene and heptane. The method of this invention can also employ an inert solvent, and thus, in one embodiment compound 3 is also contacted with an inert solvent, preferably heptane or toluene. A particular advantage of the invention, however, is that ROH independently facilitates the separation of the mixture from the acid catalyst, and thereby eliminates the need to employ an inert solvent. Thus, in another embodiment, compound 3 is not contacted with an inert solvent.

In a preferred embodiment the process is carried out in a manner in which the molar ratio of the compound of formula 3 to acid catalyst is from about 0.2 to about 50. In a more preferred embodiment the molar ratio of the compound of formula 3 to acid catalyst is from about 0.5 to about 15.0. In a still even more preferred embodiment the molar ratio of the compound of formula 3 to acid catalyst is from about 0.7 to about 2.0.

In another preferred embodiment the process is carried out in a manner that the molar ratio of the compound of formula 3 to compound ROH and/or RCOOH is from about 0.05 to about 20. In a more preferred embodiment the molar ratio of the compound of formula 3 to compound ROH and/or RCOOH is from about 0.05 to about 5. In an even more preferred embodiment the molar ratio of the compound of formula 3 to compound ROH and/or RCOOH is from about 0.4 to about 5.

In still another preferred embodiment the process is carried out in a manner that the molar ratio of compound ROH and/or RCOOH to acid catalyst is from about 0.2 to about 50. In a more preferred embodiment the molar ratio of compound ROH and/or RCOOH to acid catalyst is from about 0.4 to about 20. In a further preferred embodiment the molar ratio of compound ROH and/or RCOOH to acid catalyst is from about 1 to about 5.

The process can be performed over a wide variety of conditions, and can be performed either continuously or batch-wise. Although the reaction generally proceeds regardless of the temperature, the temperature can generally be optimized to balance the speed of the reaction and the quality of the mixture. A preferred temperature range for carrying out the process is from about +11 to about 200° C., and a more preferred range of temperatures is from about 20 to about 150° C.

The method can be performed generally by preparing a mixture of acid catalyst, hydroxyl-containing compound ROH or RCOOH, and the Diels-Alder adduct 3, and stirring the mixture until sufficient conversion of the starting material is reached. The catalyst and the hydroxyl-containing compound ROH can then be separated from the product, and the product distilled for further purification.

The term "sufficient conversion," in the specific case of said mixtures of isomeric compounds 1 and 2, usually means that the concentration of unreacted Diels-Alder adduct 3 is close to or below 2%. However, in some cases it may be advantageous to stop the process before achieving this conversion, which may provide a mixture with higher content of the 2a-γ isomer.

A possible mechanism of the positive effect of the hydroxyl-containing additives in accordance with the present invention follows and is shown in Scheme 7. In the presence of the hydroxyl-containing compound ROH or RCOOH, a portion of starting material 3 reacts reversibly with ROH or RCOOH and gives a derivative 12-R (where R≠H) which is unable to cyclize into 1a-α, 1a-β, 1a-γ, thus "leaving more time" for protonation of the endocyclic double bond, and subsequent transformations into 13, 9, and further into 2a-γ, 2a-β, 2a-α. Also, when aqueous acids are used as catalysts, the hydroxyl-containing compound promotes the formation of hydroxy derivative 12-H (where R=H) which reacts similarly.

In the course of the cyclization, intermediates 12-R, 12-H, 13-R, and 13-H can be observed by GLC. We have isolated the intermediates 12a-R, where R=$R^1$=$R^2$=$R^3$=Me, and 12a-H, where R=H, and $R^1$=$R^2$=$R^3$=Me, and experimentally proved their capability to give increased amounts of the 2a-γ isomer under the cyclization conditions. Intermediate 12a-R reacts slower than 12a-H but gives better results.

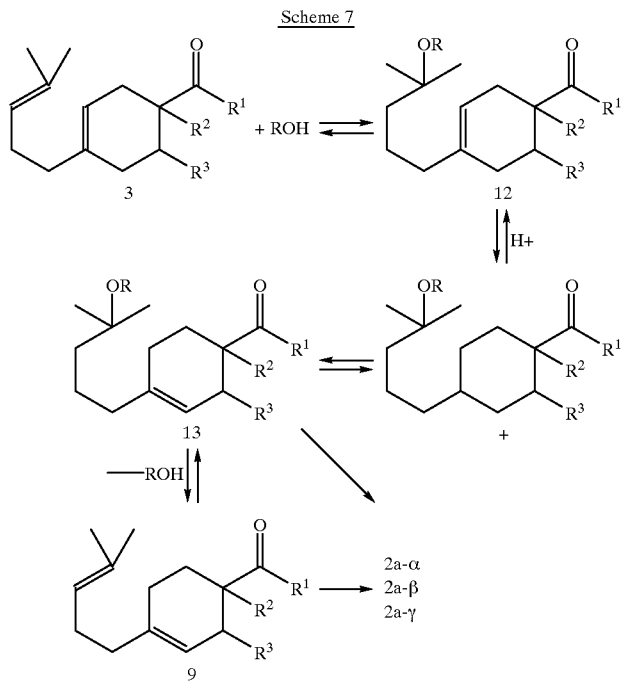

Scheme 7

In one embodiment the reaction conditions are changed during the reaction in such a way as to achieve a higher concentration of the reactive intermediate 12 in the earlier stage of the reaction, and then sufficient conversion of the reactive intermediate 12 into isomeric acyloctahydronaphthalenes 1 and 2 in the final stage of the reaction. Thus, in a preferred embodiment the method further comprises the consecutive steps of implementing reaction conditions that favor formation of the compound of formula 12, and 13, and subsequently implementing process conditions that favor formation of the compounds of formulas 1 and 2.

In a second independent embodiment intermediates 12 and/or 13 are isolated or concentrated and then cyclized subsequently. Thus, the invention also provides a process for obtaining isomeric compounds represented by formulas 1 and 2, comprising contacting a composition comprising a compound represented by formula 12 with an acid catalyst, wherein:

a. formulas 1, 2, and 12 are as shown below:

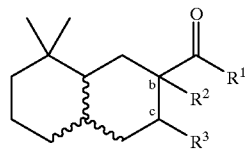

1

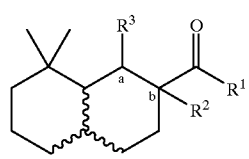

2

-continued

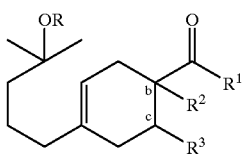

12 b. one of the wavy lines in each of formulas 1 and 2 represents a double bond, and the two other wavy lines represent a single bond;

c. R is a linear or cyclic alkyl group, or hydroxyalkyl group, or alkoxyalkyl group, or aryl group, and is substituted or unsubstituted, saturated or unsaturated;

d. $R^1$ and $R^2$ are independently hydrogen or lower alkyl;

e. $R^3$ is lower alkyl;

f. the configurations at carbon b and c in structures 1 and 12, and a and b in structure 2 are independently R or S.

The preceding discussion concerning various methods of practicing the first independent embodiment of the invention, and preferred embodiments of the invention, is generally applicable to the above second independent embodiment as well.

Experimental

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, percentage is percentage by weight, parts are parts by weight, temperature is in ° C. or is at room temperature, and pressure is at or near atmospheric.

GLC analyses were performed on a standard 30-m Stabilwax capillary column, detector-FID, carrier gas- Helium. GLC data are given after subtraction of the peaks of the solvent (if any) and of the hydroxyl-containing compound. $^1$H NMR spectra were recorded for solutions in $CDCl_3$ at 270, 300 or 500 MHz; $^{13}$C NMR spectra—at 75 MHz. Melting points were determined on a Mettler FP-50 instrument.

The examples show unequivocally that the process in accordance with the present invention results in improved quality of the cyclized product, while providing higher yields compared to the yields reported in the prior art.

ANALYTICAL EXAMPLE 1
Technique for Isolating Individual Isomers and Scheme of Their Formation In order to overcome the lack of information on the composition of mixtures of isomeric acetyloctahydronaphthalenes 1a and 2a and to correctly compare the invention and the prior art, we elaborated a special technique that allowed us to isolate the components of the mixtures and to rigorously prove their structures. Scheme 8 is based on results obtained by this method. The scheme shows the structures of isomeric acetyloctahydronaphthalenes and a simplified scheme of their formation and the interconversions occurring during the cyclization of the Diels-Alder adduct 3a (showing only one enantiomer, although, as noted previously, the enantiomers are typically present in racemic mixtures).

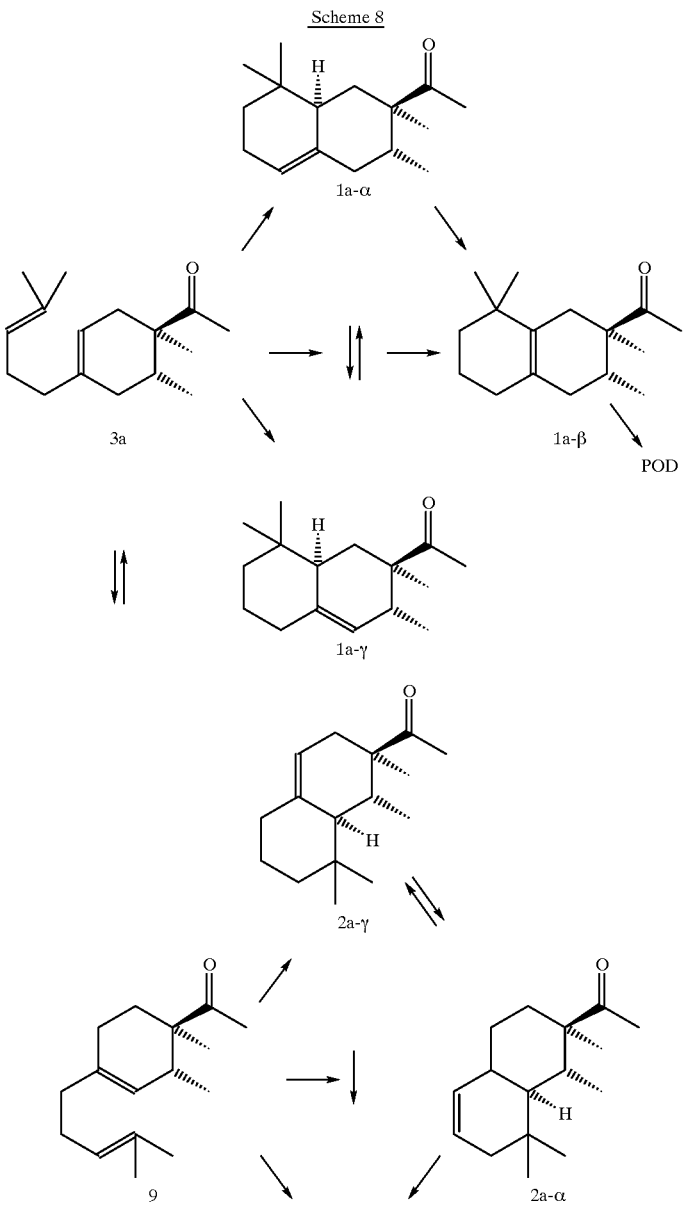

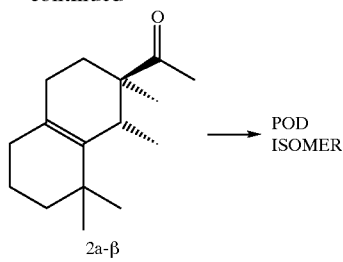

2a-β → POD ISOMER

In addition, because the composition containing Diels-Alder adduct 3a may contain structural isomer 10, shown in Scheme 9, isomer 11 is also produced during the cyclization.

Scheme 9

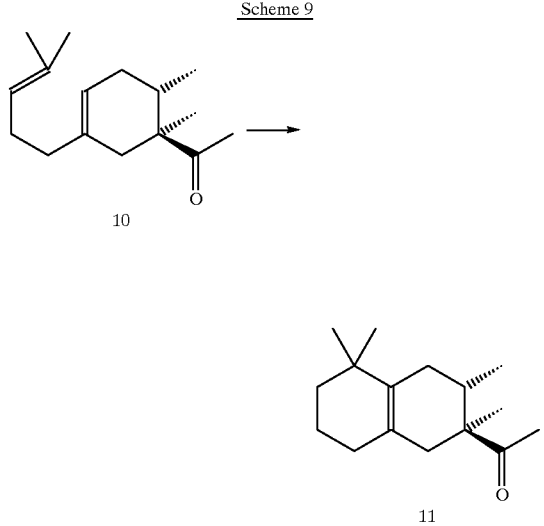

10

11

In this analytical example, we mixed 216 g of the mixture of Working Example 1 with a filtered solution prepared from 184 g of hydroxylamine sulfate, 180.6 g of 50% aq. NaOH and 2,330 g of ethanol, refluxed the mixture for 6–8 h and allowed it to cool overnight. The first portion of crystals (~60 g) was filtered off, the filtrate was diluted with water (approx. 500 ml), and a second portions of crystals (~50 g) was obtained. This sequence of operations was repeated 6–8 times using progressively smaller portions of water to give respectively 6–8 progressively smaller portions of crystals. The weight of all portions of crystals totaled ~215 g. GLC analysis of the crystallines (solutions in $CHCl_3$) showed that the initial two fractions contained predominantly 1a-β-oxime, the next two fractions contained increased amounts of 1a-γ-oxime and 1a-α-oxime, and the next fractions contained increased amounts of 2a-γ-oxime. The final fractions were richer in 2a-β-oxime and 11-oxime. Pure oximes were obtained by recrystallizing the corresponding fractions from heptane. The melting points of the pure oximes are given in Analytical Table A1-1. NMR spectra of the oximes confirming their structures are given in Analytical Tables A1-2 and A1-3. Structures of the 1a-α-oxime and 1a-γ-oxime were also confirmed by X-ray crystallography.

| Analytical Table A1-1 | | | |
|---|---|---|---|
| Compound | m.p., °C. | Compound | m.p., °C. |
| 1a-α-oxime | 134–135 | 2a-β-oxime | 128–129 |
| 1a-β-oxime | 160–161 | 2a-λ-oxime | 153–154 |
| 1a-λ-oxime | 134–135 | 11-oxime | 116–117 |

To regenerate the acetyloctahydronaphthalenes from their oximes, 1 part of an oxime was dissolved in 20 parts of boiling acetone, then 10 parts of 12–13% aq. sulfuric acid was added, and the resulting mixture was refluxed. When conversion of the oxime reached 70% or higher (GLC), acetone was evaporated, the residue was extracted with heptane, the heptane extract was washed with saturated aq. $NaHCO_3$ and with water. Heptane was evaporated, crystals of unreacted oxime were filtered off, and the filtrate was distilled to give the acetyloctahydronaphthalenes in 95–99% purity. NMR spectra for the acetyloctahydronaphthalenes obtained are given in Analytical Tables A1-4 and A1-5. The physico-chemical constants of the acetyloctahydronaphthalenes are given in Analytical Table A1-6.

Analytical Table A1-2. $^1H$ NMR spectra for oximes of acetyloctahydronaphthalenes 1a and 2a

| | Chemical shift, δ ppm ($CDCl_3$) | | | | | |
|---|---|---|---|---|---|---|
| Compound | $MeC_{quat.}$ | MeCH | MeC = N | = CH | = NOH | Others |
| 1a-α-oxime | 0.75 s; 0.87 s; 1.11 s | 0.70 d, j 6.6 Hz | 1.83 s | 5.34 br.s | 8.69 br.s | 1.45 dd, j 12.5 hz, j 4.3 Hz, 1 H |
| 1a-β oxime | 0.90 s; 0.92 s; 0.94 s | 0.72 d, j 6.5 Hz | 1.87 s | | 6.56 br. | 2.20 dm, j 16.3 Hz |
| 1a-γ oxime | 0.74 s; 0.87 s; 0.91 s | 0.76 d, j 7.3 Hz | 1.84 s | 5.07 q | 8.33 br.s | 2.17 dm, j 13.7 Hz,1 H; 2.47 m, 1 H, MeCH |
| 2a-β oxime | 0.91 s; 1.01 s; 1.04 s | 1.00 d, j 6.8 Hz | 1.77 s | | 7.53 br.s | 2.36 q, j 7 Hz, MeCH |
| 2a-γ oxime | 0.83 s; 1.00 s; 1.03 s | 0.90 d, j 6.5 Hz | 1.88 s | 5.42 d | 5.60 br. | 1.62 dd, j 16 Hz, 7 Hz |
| 11-oxime | 0.94 s; 0.95 s; 0.96 s | 0.76 d, j 6.8 Hz | 1.83 s | | 8.60 br. | 2.23 d, j 17.1 Hz, 1 H |

Analytical Table A1-3. $^{13}$C Spectra for oximes of acetyloctahydronaphthalenes 1a and 2a Chemical shift, δ ppm (CDCl$_3$)

| Compound | Me groups | C = C | C = N | CH$_2$ groups | CH groups | Quatern. |
|---|---|---|---|---|---|---|
| 1a-α oxime | 9.7; 14.4; 16.6; 23.3; 28.8 | 118.7 (=CH); 138.5 | 163.5 | 22.5; 35.8; 38.2; 39.6 | 33.1 | 33.4; 42.6 |
| 1a-β oxime | 9.8; 14.2; 16.2; 27.0; 28.1 | 125.8; 132.6 | 163.7 | 19.3; 30.7; 35.7; 37.0; 39.8 | 32.5 | 33.5; 43.2 |
| 1a-γ oxime | 9.8; 14.4; 16.1; 20.6; 29.4 | 125.7 (=CH); 136.5 | 163.9 | 22.5; 34.7; 34.8; 42.5 | 34.4; 44.3 | 34.6; 43.4 |
| 2a-β oxime | 10.8; 17.0; 25.5; 28.9; 30.0 | 127.3; 138.1 | 162.7 | 19.3; 26.7; 28.7; 31.2; 41.0 | 34.9 | 34.2; 43.4 |
| 2a-γ oxime | 10.1; 16.5; 19.2; 20.5; 31.8 | 117.5 (=CH); 139.9 | 164.0 | 24.1; 35.7; 36.3; 43.4 | 33.2; 53.6 | 37.6; 44.9 |
| 11 oxime | 9.8; 15.5; 16.1; 27.4; 28.2 | 125.0; 133.0 | 163.4 | 19.3; 30.0; 31.1; 39.5; 41.1 | 33.1 | 33.4; 42.6 |

Analytical Table A1-4 - $^1$H NMR spectra for acetyloctahydronaphthalenes 1a and 2a Chemical shift, δ ppm (CDCl$_3$)

| Compound | MeC$_{quat.}$ | MeCH | MeC = O | = CH | Others |
|---|---|---|---|---|---|
| 1a-α | 0.75 s; 0.88 s; 1.07 s | 0.68 d, j 6.2 Hz | 2.10 s | 5.35 m | 1.49 dd, j 12.2 hz, j 4.2 Hz, 1 H |
| 1a-β | 0.91 s; 0.92 s; 0.95 s | 0.75 d, j 6.7 Hz | 2.12 s |  | 1.93 dam, j 17.6 Hz; 2.27 DT, j 16.2 Hz |
| 1a-γ | 0.68 s; 0.83 s; 0.87 s | 0.68 d, j 7.3 Hz | 2.06 s | 5.00 q | 2.58 m, 1 H, MeCH |
| 2a-β | 0.98 s; 1.00 s; 1.06 s | 1.00 d, j 6.8 Hz | 2.06 s |  | 2.55 q, j 7 Hz, MeCH |
| 2a-γ | 0.82 s; 0.99 s; 1.02 s | 0.87 d, j 6.8 Hz | 2.12 s | 5.41 do | 1.69 dam, j 15 Hz; 6.8 Hz |
| 11 | 0.93 s; 0.93 s; 0.96 s | 0.78 d, j 6.8 Hz | 2.11 s |  | 2.28 d, j 17.1 Hz, 1 H |

Analytical Table A1-5 - $^{13}$C NMR spectra for acetyloctahydronaphthalenes 1a and 2a Chemical shift, δ ppm (CDCl$_3$)

| Compound | Me groups | C = C | C = O | CH$_2$ groups | CH groups | Quatern. |
|---|---|---|---|---|---|---|
| 1a-α | 13.1; 16.9; 23.1; 24.9; 28.6 | 118.8 (=CH); 137.9 | 213.1 | 22.3; 35.7; 37.5; 39.5 | 36.7; 41.6 | 30.9; 52.2 |
| 1a-β | 15.0; 16.1; 25.2; 27.0; 27.8 | 125.7; 131.9 | 213.8 | 19.1; 30.7; 34.0; 36.7; 39.5 | 32.4 | 33.3; 50.7 |
| 1a-γ | 13.7; 16.5; 20.4; 25.4; 29.3 | 125.6 (=CH); 136.2 | 214.0 | 22.3; 34.2; 34.6; 42.3 | 34.3; 43.9 | 34.5; 51.0 |
| 2a-β | 16.7; 23.5; 24.5; 28.1; 29.7 | 127.4; 139.1 | 212.5 | 18.7; 25.4; 28.5; 30.7; 40.4 | 33.8 | 34.0; 51.2 |
| 2a-γ | 15.5; 19.7; 20.0; 25.1; 31.4 | 116.4 (=CH); 140.4 | 213.7 | 23.8; 35.1; 35.9; 43.0 | 33.2; 53.35 | 37.3; 52.1 |
| 11 | 15.1; 15.9; 24.8; 27.2; 27.7 | 124.2; 132.9 | 213.5 | 19.0; 29.6; 30.9; 39.3; 39.8 | 32.8 | 33.1; 50.1 |

Analytical Table A1-6. Physico-chemical constants of acetyloctahydronaphthalenes

| Compound | B.p.,0C at ~1 mm Hg | m.p., ° C. | n$_D{}^{20}$ |
|---|---|---|---|
| 1a-α | 109–110 | 41–42 |  |
| 1a-β | 105–106 |  | 1.4981 |
| 1a-λ | 106–106.5 | 67–68 |  |
| 2a-β | 103–104 |  | 1.5030 |

-continued

Analytical Table A1-6. Physico-chemical constants of acetyloctahydronaphthalenes

| Compound | B.p.,0C at ~1 mm Hg | m.p., ° C. | $n_D^{20}$ |
|---|---|---|---|
| 2a-λ | 107–109 | | 1.5037 |
| 11 | 104–105 | | 1.4969 |

Note:
acetycloctahydronaphthalenes 1a-α and 1a-λ can also be purified by the fractional distillation of the isomeric mixture obtained as in Working Example 1, followed by crystallization from distillation fractions.

Synthetic Example 1
Synthesis of the Diels-Alder Adduct 3a (a) Synthesis of 3-methyl-3-penten-2-one (MPO). Acetaldehyde (585 g) was added over a period of 0.5–1 hour to a stirred solution of 59 g of concentrated sulfuric acid in 4800 g of 2-butanone, and the resultant solution was gradually heated to 73–78° C., while maintaining a reasonably moderate reflux. The mixture was refluxed at this temperature until the concentration of MPO reached 20% (GLC), then cooled to ambient temperature, neutralized by any conventional method, and distilled to give 3940 g of unreacted 2-butanone and 694 g of 3-methyl-3-penten-2-one (MPO), b.p. 64–66° C. (~50 mm Hg).

(b) Synthesis of 1-[1,6-dimethyl-3-(4-methyl-3-pentenyl)-3-cyclohexen-1-yl]ethanone (Diels-Alder adduct 3a). To a cooled solution of 12–14 g of boron trifluoride gas in 544 g of 3-methyl-3-penten-2-one (MPO) was added 1200 g of commercial myrcene (76–78% purity) slowly enough to maintain the reaction temperature within the 10–14° C. interval. Then, the mixture was stirred at this temperature until the concentration of unreacted MPO fell below 8%, then neutralized by conventional methods, washed and distilled to give 1045 g of the Diels-Alder adduct which contained over 90% of 1-[1,6-dimethyl-3-(4-methyl-3-pentenyl)-3-cyclohexen-1-yl]ethanone (formula 3a) and less than 10% of other isomers. $^1$H NMR (CDCl$_3$, 270 MHz): δ0.78 d, 6 Hz, Me—C$^6$; 0.95 s, Me—C$^1$; 1.57 s and 1.65 br.s, Me$_2$C=; 2.11 s, MeCO; 5.04 m, HC= in side chain; 5.31 m, HC= in cyclohexene.

Synthetic Example 2
Synthesis of the Diels-Alder Adduct 3b ($R^1=R^2=H$; $R^3=Me$)

A mixture of 220.9 g of crotonaldehyde and 554.6 g of myrcene (purity 90%+) was added over a period of 6 hours at 5–15° C. to a stirred solution of 30 g of BF$_3$ etherate in 150 ml of toluene. The mixture was neutralized by conventional methods, washed and distilled to give 248.1 g of the Diels-Alder adduct (b.p. 95–101° C. at ~2 mm Hg), which contained over 90% of 6-methyl-4-(4-methyl-3-pentenyl)-3-cyclohexene-1-carboxaldehyde 3b and less than 10% of other isomers. Odor: floral, citrus (orange-like), slightly green.

Synthetic Example 3
Synthesis of the Diels-Alder Adduct 3c ($R^1=Et$; $R^2=H$; $R^3=Me$)

Commercial myrcene (purity 76–78%; 104.3 g) was added over a period of 0.5 h at 2–8° C. to a stirred solution of 1.6 g of BF$_3$ gas in 49.1 g of 4-hexen-3-one. The mixture was stirred at 2–8° C. for 1.5 h, then neutralized by conventional methods, washed and distilled to give 72.7 g of the Diels-Alder adduct (b.p. 107–117° C. at ~2 mm Hg), which contained over 80% of 1-[6-methyl-4-(4-methyl-3-pentenyl)-3-cyclohexen-1-yl]-1-propanone 3c and less than 20% of other isomers.

Synthetic Example 4
Synthesis of the Diels-Alder Adduct 3d ($R^1=H$; $R^2=Me$; $R^3=Et$)

A mixture of 500 g of 2-methyl-2-pentenal and 1060 g of myrcene (purity 90%+) was added over a period of 2 hours at 8–15° C. to a stirred solution of 61 g of BF$_3$ etherate in 500 ml of toluene. The mixture was stirred 2.5 h at 8–15° C., then neutralized by conventional methods, washed and distilled to give 791 g of the Diels-Alder adduct (b.p. 130–132° C. at ~2 mm Hg), which contained over 84% of 6-ethyl-1-methyl-4-(4-methyl-3-pentenyl)-3-cyclohexene-1-carboxaldehyde 3d and less than 16% of other isomers.

Working Example 1
Cyclization of Diels-Alder Adduct 3a in the Presence of Phosphoric Acid and Methanol The Diels-Alder adduct 3a (120 g) was added over a period of 10 min at 70–85° C. to a stirred mixture of 60 g of 85% aqueous phosphoric acid and 30 g of methanol. The mixture was stirred at 92–98° C. (moderate reflux) and periodically sampled for GLC analysis. The progress of the reaction is illustrated in Table W1-1 which shows how concentrations of the major components change vs. time.

TABLE W1-1

Concentration of major components[a] 1, 2, 3, 9, 10, 11, and 12 in the reaction mixture, %[b]

| Time, hours | 11 | 1a-β | 2a-β[c] | 1a-γ | 9 + 10[d] | 3a | 2a-γ | 1a-α | 12a-R | 12a-H |
|---|---|---|---|---|---|---|---|---|---|---|
| 0[e] | | | | | 4.3 | 91.2 | | | | |
| 1 | 1.4 | 24.4 | 0.6 | 12.6 | 5.7 | 20.7 | 2.2 | 12.7 | 8.9 | 1.0 |
| 2 | 2.0 | Σ 35.2 | | 0.6 | 4.9 | 10.4 | 4.5 | 13.3 | 4.1 | 0.4 |
| 3 | 2.3 | 38.3 | 2.6 | 17.1 | 3.7 | 6.1 | 5.7 | 13.3 | 2.6 | 0.3 |
| 4 | 2.6 | 43.1 | 3.0 | 17.6 | 2.6 | 3.6 | 6.2 | 12.7 | 1.3 | 0.1 |

TABLE W1-1-continued

Concentration of major components[a] 1, 2, 3, 9, 10, 11, and 12 in the reaction mixture, %[b]

| Time, hours | 11 | 1a-β | 2a-β[c] | 1a-γ | 9 + 10[d] | 3a | 2a-γ | 1a-α | 12a-R | 12a-H |
|---|---|---|---|---|---|---|---|---|---|---|
| 5 | 2.7 | 45.7 | 3.9 | 17.5 | 1.9 | 2.4 | 6.3 | 12.2 | 0.9 | <0.1 |
| 5.5 | 2.8 | 45.8 | 5.3 | 17.4 | 1.7 | 1.9 | 6.4 | 12.0 | 0.8 | — |

Notes:
[a]Numeration of compounds is the same as elsewhere in the text of this document.
[b]Determined by GLC.
[c]Peak of 2a-β is a shoulder on the peak of 1a-β.
[d]Peaks co-elute.
[e]Starting material.

After 5.5 hours, the mixture was cooled to about 40° C., the layers were separated, and the bottom phosphoric acid/methanol layer (85.5 g) was reused as will be shown below. The organic layer was diluted with 100 ml of heptane, washed with minimal amounts of 10% aqueous NaOH and water, filtered, evaporated and distilled to give 115.75 g (yield 96.5% of theory) of a mixture of isomers with the following composition (%):

TABLE W1-2

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.07 | 2.9 | 47.1 | 5.2 | 17.5 | 1.5 | 1.8 | 6.3 | 11.8 |

The mixture possessed a strong amber-woody odor.

The weight of the acid-methanol layer was brought to 90 g by addition of 2.5 g of phosphoric acid and 2.0 g of methanol, and the resultant solution was used again as the catalytic system for the cyclization of another 120-g portion of the Diels-Alder adduct 3a as described above. The whole sequence of operations was repeated many times without loss of yield of the cyclized product and without significant changes in its composition.

Comparative Example 1-A

Cyclization of Diels-Alder Adduct 3a in the Presence of Phosphoric Acid and Toluene According to the Procedure of U.S. Pat. Nos. 3,907,321, 3,911,018, and 3,929,677

The Diels-Alder adduct 3a (120 g) was added over a period of 45 min at 72–78° C. to a vigorously stirred mixture of 60 g of 85% aqueous phosphoric acid and 60 g of toluene. The mixture was stirred at this temperature and sampled for GLC. The course of reaction is illustrated in Comparative Table 1-1 which shows how concentrations of the major components change vs. time.

Comparative Table 1-1

Concentration of major components[a] 1a, 2a, 3a, 9, 10, 11, 12 and POD in the reaction mixture, %[b]

| Time, hours | 11 | 1a-β | 2a-β[c] | 1a-γ | 9 + 10[d] | 3a | 2a-γ | 1a-α | 12a-H | POD & its isomer |
|---|---|---|---|---|---|---|---|---|---|---|
| 0[e] | | | | | | 4.3 | 91.2 | | | |
| 1 | 2.7 | 45.3 | 2.8 | 7.1 | 2.1 | 27.2 | 0.5 | 8.5 | | 1.5 |
| 2 | 3.6 | 62.3 | | 8.2 | 1.1 | 10.7 | 0.5 | 8.1 | — | 2.4 |
| 3 | 4.0 | 69.4 | | 8.2 | 0.6 | 4.1 | 0.4 | 7.2 | — | 3.1 |
| 4 | 4.3 | 73.2 | | 7.7 | 0.3 | 1.5 | 0.4 | 6.1 | — | 3.8 |
| 5 | 4.3 | 75.1 | | 7.2 | 0.1 | 0.5 | 0.3 | 5.2 | — | 4.3 |
| 5.5 | 4.3 | 75.2 | | 6.8 | 0.1 | 0.3 | 0.3 | 4.8 | — | 4.7 |

Notes:
[a]Numeration of compounds is the same as elsewhere in the text of this document.
[b]Determined by GLC.
[c]Peak of 2a-β is a shoulder on the peak of 1a-β.
[d]Peaks co-elute.
[e]Starting material.

After neutralization as in Working Example 1 and removal of toluene, the product was distilled to give 104.6 g (87.2% of theory) of a mixture of isomers with the composition (%):

Comparative Table 1-2

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 3.9 | 4.4 | Σ 76.2 | | 7.0 | 0.1 | 0.3 | 0.3 | 4.8 |

The mixture had a woody odor with an amber note much weaker than the mixture in Working Example 1.

Comparative Example 1-B
Cyclization of Diels-Alder Adduct 3a in the Presence of Phosphoric Acid and Toluene at 92–98° C.

The process was performed as in Comparative Example 1 but at 92–98° C. The course of the reaction is illustrated in Comparative Table 1-3.

Comparative Table 1-3

Concentration of major components[a] 1a, 2a, 3a, 9, 10, 11, 12 and POD in the reaction mixture, %[b]

| Time, hours | 11 | 1a-β | 2a-β[c] | 1a-γ | 9 + 10[d] | 3a | 2a-γ | 1a-α | 12a-H | POD & isomer |
|---|---|---|---|---|---|---|---|---|---|---|
| 0[e] | | | | | 4.9 | 91.6 | | | | |
| 0.5 | 2.8 | 49.9 | | 7.3 | 1.9 | 22.5 | 0.5 | 8.9 | 0.06 | 1.3 |
| 1 | 3.8 | 64.6 | | 8.1 | 0.8 | 6.4 | 0.4 | 7.5 | — | 4.1 |
| 1.7 | 4.2 | 73.0 | | 6.9 | 0.1 | 0.5 | 0.2 | 4.8 | — | 6.1 |

Notes:
[a]Numeration of compounds is the same as elsewhere in the text of this Application.
[b]Determined by GLC.
[c]Peak of 2a-β is a shoulder on the peak of 1a-β.
[d]Peaks co-elute.
[e]Starting material.

After neutralization as in Working Example 1 and removal of toluene, the product was distilled to give 107.8 g (89.85% of theory) of a mixture of isomers with the composition (%):

Comparative Table 1-4

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 6.1 | 4.3 | Σ 73.0 | | 6.9 | 0.1 | 0.5 | 0.2 | 4.8 |

The mixture had a woody odor with an amber note much weaker than the mixture obtained in Working Example 1.

Working Example 2
Cyclization of the Diels-Alder Adduct 3a in the Presence of Sulfuric Acid and Methanol The Diels-Alder adduct 3a (60 g) was added over a period of 7 min at 55–60° C. to a stirred mixture of 30 g of 62% aqueous sulfuric acid and 30 g of methanol. The mixture was stirred at 72–78° C. In four hours, the concentration of the starting material 3a dropped below 2% (GLC), the mixture was cooled, and the layers were separated. The organic layer was diluted with heptane, neutralized and washed. After evaporation of heptane, the product was distilled to give 55.06 g (91.8% yield) of a mixture of isomers with the following composition (%):

TABLE W2-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.16 | 3.1 | 57.2 | 7.7 | 10.7 | 1.5 | 1.9 | 7.4 | 5.2 |

The mixture possessed a strong amber-woody odor.

Comparative Example 2
Cyclization of the Diels-Alder Adduct 3a in the Presence of Sulfuric Acid and Toluene According to the Procedure of U.S. Pat. Nos. 3,907,321, 3,911,018, and 3,929,677

The Diels-Alder adduct 3a (84 g) was added over a period of 45 min at 55–60° C. to a stirred mixture of 50 g of 62% aqueous sulfuric acid and 50 g of toluene. The mixture was then vigorously stirred 6 hours at 72–78° C., cooled, and the layers were separated. The organic layer was neutralized and washed. After evaporation of heptane, the product was distilled to give 61.5 g (73.2% yield) of a mixture of isomers with the following composition (%):

Comparative Table 2-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 4.5 | 4.5 | 74.9 | 7.4 | 3.4 | 0.1 | 0.4 | 0.5 | 1.7 |

The mixture possessed a woody odor with amber note much weaker than the mixture obtained in Working Example 2.

Working Example 3
Cyclization of the Diels-Alder Adduct 3a in the Presence of Boron Trifluoride Etherate and Methanol The Diels-Alder adduct 3a (50.4 g) was added at below 25° C. to a stirred solution of 30 g of boron trifluoride etherate in 100 g of anhydrous methanol under dry nitrogen, and the stirred mixture was then refluxed at 61–62° C. for 4.5 h. The resulting mixture, which contained over 66% of the reactive intermediate 12a-R (GLC, methanol not integrated), was diluted with 100 g of heptane, and carefully, in 6 portions, evaporated at 62–78° C. (pot temperature) until the total amount of the distillate reached 165 g. During this process, composition of the reaction mixture changed as shown in Table W3-1.

TABLE W3-1

| Stage of the process | Concentration of major components, % (GLC) | | | | | | | | |
|---|---|---|---|---|---|---|---|---|---|
| | 11 | 1a-β | 2a-β | 1a-γ | 9 + 10 | 3a | 2a-γ | 1a-α | 12a-R |
| Starting material | | | | | 5.0 | 90.3 | | | |
| After 4.5 h at 61–62° C. | | 2.5 | | 1.7 | 1.9 | 15.3 | | 2.8 | 66.3 |
| During: | | | | | | | | | |
| Evaporation at 62–65° C. | 0.2 | 2.9 | | 2.0 | 1.1 | 16.0 | | 3.5 | 64.0 |
| Evaporation at 65–68° C. | 0.2 | 3.5 | | 2.3 | 1.3 | 17.4 | | 3.8 | 62.9 |
| Evaporation at 68–71° C. | 0.3 | 5.5 | | 3.1 | 1.7 | 17.9 | 0.1 | 5.1 | 54.2 |
| Evaporation at 71–74° C. | 1.3 | 22.3 | | 8.8 | 4.4 | 16.4 | 2.0 | 10.4 | 20.9 |
| Evaporation at 74–76° C. | 2.5 | 42.0 | 2.8 | 13.3 | 2.5 | 4.2 | 5.1 | 12.4 | 5.6 |
| Evaporation at 76–78° C. | 2.6 | 43.9 | 3.3 | 13.6 | 1.8 | 2.9 | 5.2 | 12.3 | 5.4 |
| After evaporation | 3.0 | 49.1 | 4.9 | 13.7 | 1.4 | 1.7 | 5.0 | 11.6 | 1.9 |

The mixture was diluted with heptane, quenched with an excess of 30% NaOH at below 40° C., washed with water, filtered, evaporated and distilled to give 45.7 g (yield 90.7%) of a mixture of isomers with the following composition (%):

TABLE W3-2

| Isomer | 11 | 1a-β | 2a-β | 1a-γ | 9 + 10 | 3a | 2a-γ | 1a-α |
|---|---|---|---|---|---|---|---|---|
| % | 3.1 | 49.7 | 5.1 | 13.7 | 1.4 | 1.6 | 5.0 | 11.3 |

Comparative Example 3
Cyclization of the Diels-Alder Adduct 3a in the Presence of Boron Trifluoride Etherate in Toluene According to the Procedure of U.S. Pat. Nos. 3,907,321, 3,911,018, and 3,929,677

The Diels-Alder Adduct 3a (50 g) was added over a period of 50 min at below 25° C. to a stirred solution of 29.5 g of boron trifluoride etherate in 200 g of toluene under dry nitrogen. The mixture was stirred 13 hours at 48–51° C. and periodically sampled for GLC. The course of the reaction is illustrated in Comparative Table 3-1.

Comparative Table 3-1

Concentration of major components 1a, 2a, 3a, 9, 10, 11 in the reaction mixture, %

| Time, hours | 11 | 1a-β | 2a-β | 1a-γ | 9 + 10 | 3 | 2a-γ | 1a-α |
|---|---|---|---|---|---|---|---|---|
| 0 | | | | | 5.0 | 90.3 | | |
| 4 | 2.4 | Σ 38.2 | | 6.9 | 5.2 | 27.2 | 0.8 | 14.7 |
| 7 | 3.2 | 49.1 | 2.1 | 8.5 | 3.3 | 11.3 | 1.2 | 16.0 |
| 8 | 3.5 | 52.9 | 2.9 | 9.0 | 2.4 | 6.7 | 1.2 | 16.3 |
| 10 | 3.7 | 55.5 | 3.6 | 9.3 | 1.7 | 3.9 | 1.2 | 16.0 |
| 11 | 3.8 | 57.0 | 4.0 | 9.4 | 1.3 | 2.7 | 1.1 | 15.8 |
| 13 | 3.9 | 59.2 | 4.5 | 9.4 | 0.8 | 1.4 | 0.9 | 15.0 |

After neutralization, removal of toluene and distillation, the product (41.2 g; yield 82.4%) contained:

Comparative Table 3-2

| Isomer | 11 | 1a-β | 2a-β | 1a-γ | 9 + 10 | 3a | 2a-γ | 1a-α |
|---|---|---|---|---|---|---|---|---|
| % | 4.0 | 59.8 | 4.4 | 9.3 | 0.7 | 1.1 | 0.8 | 14.3 |

The product had a woody odor with an amber note much weaker than the product obtained in Working Example 3.

Working Example 4

Cyclization of the Diels-Alder Adduct 3a in the Presence of 5-sulfosalicylic Acid and Methanol 100 g of the Diels-Alder adduct 3a was added at 23° C. to a stirred solution of 55.9 g of 5-sulfosalicylic acid dihydrate in 44.7 g of water and 34 g of methanol. The mixture was refluxed at 84–92° C. for 15 h, worked-up and distilled to give 91.8 g (weight yield 91.8%) of a mixture with the following composition (%):

TABLE W4-1

| Isomer | 11 | 1a-β | 2a-β | 1a-γ | 9 + 10 | 3a | 2a-γ | 1a-α | 12a-R | 13a-R |
|---|---|---|---|---|---|---|---|---|---|---|
| % | 2.5 | 41.2 | 3.0 | 13.1 | 5.2 | 8.6 | 7.4 | 7.1 | 2.1 | 1.5 |

In addition, small amount of a higher boiling fraction was obtained (b.p. 122–132° C./2 mm, 4.2 g) which contained (%):

TABLE W4-2

| Isomer | 11 | 1a-β | 2a-β | 1a-γ | 9 + 10 | 3a | 2a-γ | 1a-α | 12a-R | 13a-R | 12a-H | 13a-H |
|---|---|---|---|---|---|---|---|---|---|---|---|---|
| % | 0.6 | 13.4 | 0.6 | 5.3 | 5.0 | 9.1 | 3.6 | 6.0 | 18.7 | 13.2 | 7.6 | 4.7 |

Working Examples 5–28

Cyclization of the Diels-Alder Adduct 3a in the Presence of Phosphoric Acid and Various Hydroxyl-containing Compounds General procedure: The Diels-Alder adduct 3a (60 g) was added over a period of 5–10 min to a stirred mixture of phosphoric acid and a hydroxyl-containing compound. Concentration of the acid and quantities of the components are given in Table 5. The mixture was stirred at the given temperature (Table W5-1) until the GLC analysis showed that concentration of the unreacted 3a is close to 2%, or below. Corresponding reaction times and concentrations of the desirable 2a-γ isomer are given in Table W5-1.

Working Example 29

Cyclization of the Diels-Alder Adduct 3a in the Presence of Phosphoric Acid, Methanol and Heptane (Inert Solvent)

A solution of 120 g of the Diels-Alder adduct 3a in 80 g of heptane was added over a period of 10 min at 70–80° C. to a stirred mixture of 60 g of 85% aqueous phosphoric acid and 30 g of methanol. The mixture was stirred at 80–85° C. (reflux) and periodically sampled for GLC analysis. The composition of the mixture after 14 h of reflux was (%):

TABLE W29-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.13 | 3.2 | 45.5 | 6.2 | 16.5 | 2.0 | 2.9 | 5.9 | 11.8 |

TABLE W5-1

| | Phosporic acid | | Hydroxyl-containing additive | | Reaction conditions | | |
|---|---|---|---|---|---|---|---|
| Ex. # | % | Quantity, g | Name | Quantity, g | Temp., ° C. | Time h | 2a-γ, % |
| 5 | 85 | 30 | methanol | 21 | 94–95 | 14 | 6.9 |
| 6 | 85 | 30 | methanol | 10 | 92–98 | 1 | 5.2 |
| 7 | 85 | 30 | methanol | 7.5 | 93–97 | 0.75 | 3.2 |
| 8 | 85 | 20 | methanol | 10 | 93–97 | 7 | 5.9 |
| 9 | 85 | 40 | methanol | 20 | 93–97 | 5 | 6.6 |
| 10 | 85 | 5 | methanol | 2.5 | 93–97 | 6 | 3.7 |
| 11 | 85 | 2.5 | methanol | 2.5 | 93–97 | 14 | 4.8 |
| 12 | 73 | 35.1 | methanol | 15.2 | 93–97 | 23.5 | 7.0 |
| 13 | 78 | 32.5 | methanol | 15.0 | 92–98 | 13 | 6.6 |
| 14 | 98 | 25.7 | methanol | 15.2 | 92–98 | 2 | 5.4 |
| 15 | 85 | 30 | methanol | 4.0 | 25–33 and 55–65 | 35 and 1.7 | 5.7 |
| 16 | 85 | 30 | ethanol | 30 | 98–99 | 11 | 4.5 |
| 17 | 85 | 30 | ethanol | 14.9 | 103–110 | 0.5 | 4.2 |
| 18 | 85 | 15.1 | ethanol | 15.1 | 100–105 | 9.25 | 5.1 |
| 19 | 85 | 30 | ethanol | 20 | 100–105 | 2.5 | 5.0 |
| 20 | 85 | 30.05 | ethanol | 15.35 | 90–92 | 2.2 | 5.1 |
| 21 | 85 | 30 | 1-propanol | 30 | 114–115 | 3.5 | 5.3 |
| 22 | 85 | 30 | 1-propanol | 15 | 92–98 | 1 | 4.8 |
| 23 | 85 | 30 | 2-propanol | 30 | 105–106 | 8.5 | 5.4 |
| 24 | 85 | 30 | 2-propanol | 15 | 93–97 | 1 | 4.6 |
| 25 | 85 | 30 | ethylene glycol | 15 | 95–97 | 13 | 2.2 |
| 26 | 85 | 30 | propylene glycol | 15.4 | 93–97 | 5 | 3.1 |
| 27 | 85 | 30 | 2-methoxyethanol | 30 | 109–114 | 10 | 4.7 |
| 28 | 85 | 30 | acetic acid | 15.3 | 58–63 | 1.5 | 4.7 |

Working Example 30
Isolation and Cyclization of 1-{1,6-dimethyl-4-(4-methoxy-4-methylpentyl)-3-cyclohexenyl}ethanone 12a-R a) Isolation. The process of cyclization was run as in Working Example 1, but the reaction was stopped and worked up after 0.5 h of reflux. Compound 12a-R was isolated by distillation; b.p. 122–123° C. (~1 mm). $^1$H NMR (δ, CDCl$_3$): 0.795 d, 7 Hz, MeC$^6$; 0.96 s MeC$^1$; 1.10 s, Me$_2$C; 2.11 s, MeC═O; 3.14 s, MeO; 5.31 m, CH═. $^{13}$C NMR (δ, CDCl$_3$): 15.5, 15.9, 21.6, 24.6, 24.7, 32.5, 33.7, 34.2, 37.4, 39.2, 48.6, 49.8, 74.0, 117.8, 135.9, 213.1.

b) Cyclization. Compound 12a-R (68.5 g) was added over a period of 10 min at 80–85° C. to a stirred mixture of 30.8 g of 85% phosphoric acid and 17 g of methanol. The mixture was then stirred at 90–94° C. for 21 h, cooled, and the bottom acid-methanol layer was separated. The upper layer was diluted with heptane, washed with 20% NaOH, washed with water, filtered, heptane was evaporated, and the product distilled to give 59.2 g (98.3% of theory) of a mixture of isomers with the following composition (%):

TABLE W30-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.1 | 2.9 | 43.3 | 6.6 | 16.8 | 1.9 | 2.3 | 8.5 | 11.2 |

The mixture possessed a very strong amber-woody odor.

Working Example 31
Cyclization of 1-{1,6-dimethyl-4-(4-methoxy-4-methylpentyl)-3-cyclohexenyl}ethanone 12a-R The process was carried out as in Working Example 30, but the amounts of reagents were: 12a-R-20 g, phosphoric acid-10 g, methanol-5 g. After ~8 h of reaction, the mixture contained (%):

TABLE W31-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.1 | 2.8 | 39.0 | 6.6 | 16.9 | 2.8 | 3.6 | 9.2 | 11.3 |

Working Example 32
Isolation and Cyclization of 1-{1,6-dimethyl-4-(4-hydroxy-4-methylpentyl)-3-cyclohexenyl}ethanone 12a-H a) Isolation. Compound 12a-H was isolated by distillation (b.p. 149–154° C./~1.5 mm) from a mixture obtained by hydration of 3a with aqueous phosphoric acid at reduced temperature (+2–+14° C.) for 48 h. $^1$H NMR (δ, CDCl$_3$): 0.785 d, 7 Hz, MeC$^6$; 0.96 s, MeC$^1$; 1.18 s, Me$_2$C; 2.12 s, MeC═O; 5.32 m, CH═. $^{13}$C NMR (δ, CDCl$_3$): 15.6, 16.0, 22.1, 24.9, 29.0, 29.1, 32.6, 33.8, 34.3, 37.5, 43.3, 50.0, 70.4, 117.9, 136.0, 213.8.

b) Cyclization. Compound 12a-H (10.4 g) was added over a period of 10 min at 80–85° C. to a stirred mixture of 5.2 g of 85% phosphoric acid and 2.6 g of methanol. The mixture was then stirred at 92–98° C. for 3.5 h, cooled, the bottom acid-methanol layer was separated. The upper layer was diluted with heptane, washed with 20% NaOH, washed with water, filtered, evaporated, and distilled to give 8.0 g (82.8% of theory) of a mixture of isomers with the following composition (%):

TABLE W32-1

| Isomer | POD and its isomer | 11 | 1a-β | 2a-β | 1a-γ | 9 + 10 | 3a | 2a-γ | 1a-α |
|---|---|---|---|---|---|---|---|---|---|
| % | 0.2 | 3.5 | 50.7 | 7.1 | 15.8 | 1.6 | 1.9 | 5.5 | 9.0 |

Working Example 33
Cyclization of the Diels-Alder Adduct 3b in the Presence of Phosphoric Acid and Methanol The Diels-Alder adduct 3b (60 g) was added over a period of 10 min at 80–95° C. to a stirred mixture of 30 g of 85% phosphoric acid and 15 g of methanol. The mixture was stirred at 95±3° C. until the concentration of the starting 3b fell below 3%, cooled, diluted with heptane and water, and the layers were separated. The organic layer was neutralized and washed. After evaporation of heptane, the product was distilled to give 53.75 g (89.6% yield) of a mixture of isomers possessing an odor which can be characterized as woody-amber.

Comparative Example 33
Cyclization of the Diels-Alder Adduct 3b in the Presence of Phosphoric Acid and Toluene The Diels-Alder adduct 3b (60 g) was added over a period of 10 min at 80–95° C. to a stirred mixture of 30 g of 85% phosphoric acid and 15 g of toluene. The mixture was stirred at 95±3° C. until the concentration of the starting 3b fell below 3%, cooled, diluted with heptane and water, and the layers were separated. The organic layer was neutralized and washed. After evaporation of heptane, the product was distilled to give 52.6 g (87.8% yield) of a mixture of isomers possessing an odor, which can be characterized as minty, very green, with cyclamenaldehyde-like notes.

Working Example 34
Cyclization of the Diels-Alder Adduct 3c in the Presence of Phosphoric Acid and Methanol The Diels-Alder adduct 3c (48.5 g) was added over a period of 5 min at 80–95° C. to a stirred mixture of 30 g of 85% phosphoric acid and 15 g of methanol. The mixture was stirred at 95±3° C. until the concentration of the starting 3c fell below 3%, cooled, diluted with heptane and water, and the layers were separated. The organic layer was neutralized and washed. After evaporation of heptane, the product was distilled to give 36.3 g (74.8% yield) of a mixture of isomers possessing a woody-orris, irone-like odor with a touch of amber.

Comparative Example 34
Cyclization of the Diels-Alder Adduct 3c in the Presence of Phosphoric Acid and Toluene The Diels-Alder adduct 3c (48.5 g) was added over a period of 5 min at 80–95° C. to a stirred mixture of 30 g of 85% phosphoric acid and 15 g of toluene. The mixture was stirred at 95±3° C. until the concentration of the starting 3c fell below 3%, cooled, diluted with heptane and water, and the layers were separated. The organic layer was neutralized and washed. After evaporation of heptane, the product was distilled to give 33.1 g (68.2% yield) of a mixture of isomers possessing an unpleasant sour, musty odor.

Working Example 35
Cyclization of the Diels-Alder Adduct 3d in the Presence of Phosphoric Acid and Methanol The Diels-Alder adduct 3d (120 g) was added over a period of 12 min at 80–95° C. to a stirred mixture of 60 g of 85% phosphoric acid and 30 g of methanol. The mixture was stirred at 95±3° C. until the concentration of the starting 3d fell below 3% (~8 hours), cooled, diluted with heptane and with water, and the layers were separated. The organic layer was neutralized and washed. After evaporation of heptane, the product was distilled to give 115.8 g (96.5% yield) of a mixture of isomers possessing a weak fruity-amber odor.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and examples which are to be considered as exemplary only, with a true scope and spirit of the invention being indicated by the following claims.

What is claimed is:

1. A process for obtaining isomeric compounds represented by formulas 1 and 2, comprising contacting a compound represented by formula 3 with an acid catalyst and an alcohol ROH, wherein:
   a. formulas 1, 2, and 3 are as shown below:

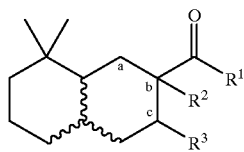

1

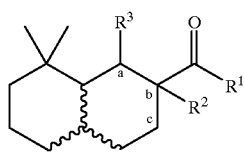

2

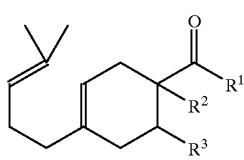

3 b. one of the wavy lines in each of formulas 1 and 2 represents a double bond, and the two other wavy lines represent a single bond;
   c. R is a linear or cyclic alkyl group, or hydroxyalkyl group, or alkoxyalkyl group, or aryl group, and is substituted or unsubstituted, saturated or unsaturated;
   d. $R^1$ and $R^2$ are independently hydrogen or lower alkyl;
   e. $R^3$ is lower alkyl; and
   f. the configuration at carbon b and c in formula 1, and a and b in formula 2, is independently R or S.

2. The process of claim 1 wherein $R^1$, $R^2$, and $R^3$ are methyl.

3. The process of claim 1 wherein the alcohol is methanol, ethanol, 1-propanol, 2-propanol, 2-alkoxyethanols, alkoxypropanols, ethylene glycol, propylene glycols, or a mixture thereof.

4. The process of claim 1 wherein the alcohol is ROH in which R is lower alkyl.

5. The process of claim 1 wherein the acid catalyst is a Brönsted acid or its solution in water.

6. The process of claim 1 wherein the acid catalyst is a Lewis acid or its complex.

7. The process of claim 1 wherein the acid catalyst is selected from the group consisting of sulfuric acid, phosphoric acid, benzenesulfonic acid, p-toluenesulfonic acid, sulfosalicilic acid, mixtures thereof, and their solutions in water.

8. The process of claim 1 wherein the contacting is carried out in the absence of an inert solvent.

9. The process of claim 1 wherein the contacting is carried out in the presence of an inert solvent.

10. The process of claim 1 wherein the molar ratio of the compound of formula 3 to acid catalyst is from about 0.2 to about 50.

11. The process of claim 1 wherein the molar ratio of the compound of formula 3 to acid catalyst is from about 0.7 to about 2.0.

12. The process of claim 1 wherein the molar ratio of the compound of formula 3 to compound ROH is from about 0.05 to about 20.

13. The process of claim 1 wherein the molar ratio of the compound of formula 3 to compound ROH is from about 0.4 to about 5.

14. The process of claim 1 wherein the molar ratio of compound ROH to acid catalyst is from about 0.2 to about 50.

15. The process of claim 1 wherein the molar ratio of compound ROH to acid catalyst is from about 1 to about 5.

16. The process of claim 1 further comprising the step of separating the acid catalyst and alcohol from compounds 1 and 2.

17. The process of claim 1 performed continuously.

18. The process of claim 1 performed batch-wise.

19. The process of claim further comprising, after contacting the compound of formula 3 with the acid catalyst and the alcohol ROH, concentrating or isolating a compound of formula 12 as shown:

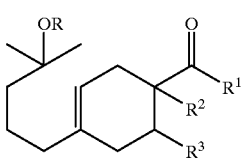

12 and contacting said concentrated or isolated compound 12 with an acid catalyst, wherein R, $R^1$, $R^2$ and $R^3$ are as defined in claim 1.

20. A process for obtaining isomeric compounds represented by formulas 1 and 2, comprising contacting a compound represented by formula 12 with an acid catalyst, wherein:
   a. formulas 1, 2, and 12 are as shown below:

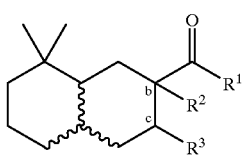

1

-continued

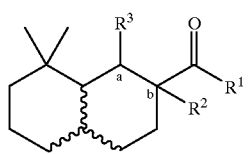

2

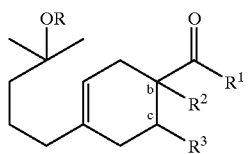

12 b. one of the wavy lines in each of formulas 1 and 2 represents a double bond, and the two other wavy lines represent a single bond;

c. R is a linear or cyclic alkyl group, or hydroxyalkyl group, or alkoxyalkyl group, or aryl group, and is substituted or unsubstituted, saturated or unsaturated;

d. $R^1$ and $R^2$ are independently hydrogen or lower alkyl;

e. $R^3$ is lower alkyl;

f. the configurations at carbon b and c in structures 1, 12, and a and b in structure 2 are independently R or S.

* * * * *

UNITED STATES PATENT AND TRADEMARK OFFICE
CERTIFICATE OF CORRECTION

PATENT NO. : 6,160,182
DATED : December 12, 2000
INVENTOR(S) : Mark B. Erman et al.

It is certified that error appears in the above-identified patent and that said Letters Patent is hereby corrected as shown below:

<u>Claim 19,</u>
Line 1, after "claim", insert -- 1 --.

Signed and Sealed this

Ninth Day of April, 2002

Attest:

JAMES E. ROGAN
*Attesting Officer*     *Director of the United States Patent and Trademark Office*